(12) United States Patent
Stier

(10) Patent No.: US 9,295,577 B2
(45) Date of Patent: Mar. 29, 2016

(54) FASTENING DEVICE FOR ORTHOSES

(75) Inventor: Gerald Stier, Langenwetzendorf (DE)

(73) Assignee: Bauerfeind AG, Zeulenroda-Triebes (DE)

( * ) Notice: Subject to any disclaimer, the term of this patent is extended or adjusted under 35 U.S.C. 154(b) by 442 days.

(21) Appl. No.: 13/817,679

(22) PCT Filed: Aug. 17, 2011

(86) PCT No.: PCT/EP2011/004125
§ 371 (c)(1),
(2), (4) Date: Apr. 12, 2013

(87) PCT Pub. No.: WO2012/022470
PCT Pub. Date: Feb. 23, 2012

(65) Prior Publication Data
US 2013/0211301 A1    Aug. 15, 2013

(30) Foreign Application Priority Data
Aug. 18, 2010  (DE) .......................... 10 2010 035 309

(51) Int. Cl.
*A61F 5/00*  (2006.01)
*A61F 5/02*  (2006.01)
*A61F 5/01*  (2006.01)

(52) U.S. Cl.
CPC ... *A61F 5/02* (2013.01); *A61F 5/01* (2013.01); *A61F 5/028* (2013.01)

(58) Field of Classification Search
CPC .............. A61F 5/00; A61F 5/01; A61F 5/02; A61F 5/028; A41F 11/16
USPC ........ 602/19, 2, 23, 24; D24/190–192; 2/311, 2/312, 319; 128/96.1, 99.1, 100.1, 101.1
See application file for complete search history.

(56) References Cited

U.S. PATENT DOCUMENTS

| 6,213,968 | B1 | 4/2001 | Heinz et al. |
| 6,322,529 | B1 | 11/2001 | Chung |
| 8,795,214 | B1 * | 8/2014 | Conti .............................. 602/19 |
| 2006/0174459 | A1 | 8/2006 | Bledsoe |
| 2009/0131841 | A1 * | 5/2009 | Epple et al. ..................... 602/19 |
| 2010/0168630 | A1 | 7/2010 | Cropper et al. |

FOREIGN PATENT DOCUMENTS

| DE | 508879 | 10/1930 |
| DE | 3814437 A1 * | 11/1989 |
| GB | 2 086 712 | 5/1982 |
| WO | WO-99/65428 | 12/1999 |

* cited by examiner

*Primary Examiner* — Kim M Lewis
(74) *Attorney, Agent, or Firm* — Jordan and Hamburg LLP

(57) ABSTRACT

A novel tightening device for orthoses for supporting and preserving the function of the human body, and more particularly for back orthoses surrounding the body, allows individual, segmental adjustment of the supporting action by way of individual, separate tackle assemblies.

17 Claims, 6 Drawing Sheets

FASTENING DEVICE FOR ORTHOSES

BACKGROUND OF THE INVENTION

The invention relates to a novel tightening device for orthoses for supporting and preserving the function of the human body, and more particularly for back orthoses surrounding the body. Orthoses are therapeutic aids used to stabilize or support the movement function of body parts, for example of the pelvis and spinal column. The use of orthoses can take place directly post-traumatically, post-operatively, or conservatively. For use, the orthoses are generally applied around the body part, for example around the hip, and closed in a belt-like manner so that a stabilizing pressure is exerted on the body region to be stabilized. In the case of lumbar orthoses, for example, it may be necessary to immobilize a particular spinal curvature (lumbar support) so as to prevent further damage to the spinal column, or to stabilize a postoperative state so as to improve the healing process.

Known orthoses, for example lumbar orthosis belts, frequently comprise tightening devices that can be used to increase the tension/pressure of the applied orthosis on the body part in a controlled manner. A tackle assembly device is frequently provided for this purpose. This is known to extend substantially over the entire width of the orthosis with the goal of equalizing the tensile force over the entire width of the orthosis belt. Known tightening devices that are based on a tackle assembly comprise a loose traction cable for this purpose, which extends toward one side of the orthosis. It has been found that orthoses having this design have shortcomings in use: the equalizing of the tensile force caused by the known tackle assembly mechanism does not allow the tension, and consequently the supporting action, to be individually adjusted to an individual treatment objective. At the same time, the tightening of known tackle assembly devices by way of cables provided on one side causes unilateral action of the force on the orthosis, and thus warping or sliding of the same.

SUMMARY OF THE INVENTION

It is the object of the invention to refine and improve tightening devices for orthoses so as to avoid the known drawbacks. The technical problem underlying the invention is that of providing an improved tightening device for an orthosis, which can be better adapted to the requirements of the therapy or prophylaxis, in particular in terms of the support function thereof. At the same time, the device is to be easier and more reliable to operate and adjust; sliding or twisting is to be prevented.

The technical problem is completely solved by a tightening device for an orthosis, which is primarily characterized by several individual, separate, in particular substantially parallel, mutually adjoining, in particular mutually directly adjoining, substantially identical tightening segments. These tightening segments can be tightened independently of each other by way of separate tackle assemblies.

Each of the tightening segments comprises a first lateral element at a first end of the tightening device and a second lateral element at an opposing second end of the tightening device. A central element is arranged in between, preferably centrally between the first and second lateral elements. The lateral elements are mechanically connected to each other via the central element, and more particularly in each case via a first tackle assembly, which runs between the central element and the first lateral element, and a second tackle assembly, which runs between the central element and the second lateral element, and thus form a tightening segment.

When donned, the tightening device, together with the orthosis, is applied around the body part, and the two ends of the tightening device are releasably connected to each other; the tightening device is closed around the body part in the manner of a belt. According to the invention, within each single tightening segment, a respective tackle assembly, which extends toward the lateral elements, is provided on both sides of a central element. When the donned orthosis is in use, the mutually opposing tackle assemblies of a tightening segment can be tensioned in a circular manner by pulling both sides of the loose ends of the two cables thereof in opposing directions. During tensioning, the distance between the lateral elements, and thus between the two ends of the tightening device, is shortened, and circular tension around the periphery of the body part is generated. Advantageously, an action of a force that is symmetrical to the central element is thus achieved. The circular tension can thus act directly, symmetrically, and uniformly on both sides of the central element, whereby the element is not displaced from the position thereof during tightening. Twisting or shifting of the tightening device or of the orthosis connected to the tightening device during tightening is effectively prevented.

In one embodiment according to the invention, a tackle assembly has multiple returns. The respective tackle assemblies are anchored on the central element and on the first or second lateral element of one and the same tightening segment. The tackle assembly of a tightening segment has no anchoring or return points at another, in particular adjoining, tightening segment. According to the invention, each tightening segment thus has a dedicated tackle assembly that is separate from the remaining tightening segments.

Deviating from the prior art, according to the invention several tackle assemblies are also independently provided, preferably substantially parallel to one another, in separate tightening segments. Each tackle assembly solely engages the associated central element and lateral elements of a tightening segment. Thus, in this embodiment, each individual tightening segment is only associated with a single individually adjustable pair of tackle assemblies. In conjunction with the opposing tackle assembly, which is directed to the other end, each tackle assembly enables a symmetrical, circular tightening action that can be individually adjusted for each segment.

So as to implement the cable drive mechanism in the form of a tackle assembly according to the invention, preferably exactly one cable return element for returning the cable of the respective tackle assembly, or, selectively or additionally, preferably exactly one anchoring point of the cable end is provided per segment toward both sides of the central element. Deviating from the prior art, the invention avoids the equalization of the action of force of a tackle assembly over larger sections, or the entire width, of the orthosis belt encountered with known multiple cable return elements or anchoring points of the cable that are located next to each other. Rather, the tackle assembly according to the invention preferably has exactly one respective anchoring point with the central element and the lateral element of the tightening segment; the anchoring point is designed in each case as a cable return element, preferably as a return roller, or as an anchoring point, in which the cable is fixed in a stationary manner. According to the invention, in each tightening segment, a force is thus exerted via the tackle assembly in a single force application point. Depending on the design of the tackle assembly, the force application point is a cable deflection point, or alternatively or additionally, a cable anchoring point. According to a special embodiment of the invention, at least two mutually spaced optional anchoring points are provided on the central element and/or lateral element, which can each be selected as alternative force application points so as to individually adjust the tightening device.

In a special embodiment, the tightening device comprises at least two, preferably three, four, or five, tightening segments that can be separately tightened. Preferred variants comprise exactly three, four, or five mutually adjoining tightening segments, each being associated with a tackle assembly pair. These variants can thus be separately tightened on three, four, or five segments.

The segmental introduction of the force into a single force application point within a segment allows a force to be introduced with vertebra segment accuracy, especially in connection with the use of the tightening device on or in a back orthosis. In this embodiment of the invention, at least one vertebra or a vertebrae group is preferably associated with a tightening segment. Preferably a single tightening segment causes a predominant action of force on or in the region of exactly one vertebra or vertebra section, and another tightening segment causes a predominant action of force on or in the region of exactly one other vertebra or vertebra section.

In addition, according to a special embodiment, at least one tightening segment, preferably on or in the region of the central element thereof, is additionally provided with at least one pad that faces the body part and is preferably made of elastic padding material, for the segmental action of force in accordance with the invention. This pad is preferably designed so as to direct the action of force of this tightening segment deliberately to a defined body region. In a preferred variant, the pad can be individually attached to or removed from the tightening device. The shape and/or material of the pad on the tightening segment can preferably be replaced and/or adjusted so as to modify the effect of the transfer of the action. In a special variant, a tightening segment may be associated with a pad that individually massages and stimulates certain soft tissue structures of the body part in conjunction with the deliberately adjustable action of force of the tightening segment. For example, a trigger point of a muscle can thus be deliberately stimulated so as to achieve targeted tension or relaxation of the muscle. It is not possible to achieve such effects on the body part that can be segmentally adjusted and triggered in a targeted manner by known orthoses that can be tightened.

In a preferred embodiment, the central element comprises both a cable anchoring point for the cable and a cable return point as a second return for the tackle assembly at a force application point. In corresponding fashion, the lateral elements comprise a cable return for returning the cable as a force application point, so as to form a triple tackle assembly. Of course, the invention also relates to other specific embodiments of tackle assemblies comprising an anchoring point and one or more return points. If several cable returns are provided at the one force application point of the tightening segment, either on the central element or on the lateral element, the returns, designed as stacked return rollers having a common axis, preferably form a roller block in the single force application point.

In addition, in a special embodiment, at least two adjoining tightening elements of the tightening device are mechanically connected to each other. To this end, preferably a rigid coupling is provided. As an alternative, a flexible coupling is preferred, notably in form of a flexible, for example elastic, band. In a special embodiment thereof, at least the lateral elements of two directly adjoining segments are mechanically connected to each other so as to form at least one integral lateral bridge made of at least two lateral elements. In a special embodiment, the lateral elements of all segments that are present are connected to each other in this way to form a single lateral bridge. The lateral bridges are integrally designed in a special variant.

In a special embodiment thereof, either as an alternative or an addition, at least the central elements of two directly adjoining segments are mechanically connected to each other so as to form at least one integral central bridge made of at least two central elements. In a special embodiment, the central elements of all segments that are present are connected to each other in this way to form a single central bridge. The central bridge can be integrally designed.

In a special embodiment, the integral central bridge additionally comprises, or consists of, at least one support element that is for a body part and that extends perpendicular to the direction of force of the tackle assembly. This support element is formed on or in, or in particular as, the central element. The support element is made of a comparatively inelastic, tough, and brittle material. The support element can be designed in form of a simple rod, for example as a metal rod that can be individually shaped or as a plastic rod that can be thermoplastically molded. Because the tightening force can be exerted in segments according to the invention, this support element can be individually applied to the body part so as to make the supporting function, or the therapeutic shaping function, possible. This support element is in particular shaped in an anatomically and therapeutically expedient manner and is directly used to support a body part, notably the spinal column, which is to say in the example of a back orthosis, the support element runs along the spinal column and thus serves to support the same.

As an alternative, instead of a single support rod, two mutually spaced, rod-shaped support elements are provided, which are connected to each other by way of transverse bridges that are formed between cutouts of the central element. Especially in the case of a back orthosis, the spinal column can thus be supported directly to the left and right of the vertebral crests; direct compressive stress on the crests is avoided.

According to the invention, the cables of the tackle assembly of a first tightening segment are each guided together, but separately and mutually spaced from the cables of the tackle assembly of an adjoining second segment. In a special embodiment, a lattice frame is provided for this purpose, which is disposed in each case between the central elements and lateral elements and holds the cables of a tackle assembly together, but in each case separately from the cables of another tackle assembly at a distance from each other. The cables are passed through the loops of the lattice frame for this purpose. To this end, especially in the case of a back orthosis, the lattice frame is preferably also designed as a stabilizing pelvic frame, which has a rotationally stabilizing effect at the same time.

In a special embodiment of the invention, the cables of a tackle assembly are guided in a cable tunnel. The cable tunnel preferably extends between the lateral element and the central element. The cable tunnel is preferably made of a plastic, flexible material; an elastic knitted fabric is particularly preferred. The invention thus allows a compact and user-friendly implementation of the segmental individual tackle assemblies. This effectively prevents cables of adjoining tackle assemblies from being brought in contact with each other and entangling with articles of clothing or other components of the orthosis.

In a special variant of this embodiment, the cable tunnel additionally comprises a tunnel branch, which branches off over the course between the lateral element and central element. The respective loose end of the cable of a tackle assembly can be guided therein. The loose end can be guided through the tunnel branch, which can be produced from plastic or flexible material in a similar manner to the cable tunnel, so that the risk of becoming twisted or knotted with the cable ends of adjoining tackle assemblies is prevented and the use of the tightening device during donning and tightening is simplified. In an alternative or additional embodiment, the cables of the tackle assemblies are each guided separately in a knitted spacer fabric.

In a special embodiment, the cables are inserted directly in the knitted fabric of an orthosis. For this purpose, the knitted fabric of the orthosis preferably comprises tunnel-like cut-outs or tabs, which allow the cables to be guided separately. Additional measures, such as the lattice frame that is provided in the previous embodiment, for arranging the cables of adjoining tackle assemblies at a distance from each other are not needed in this embodiment. In the simplified embodiment of a tightening device according to the invention that is already integrated in the knitted orthosis, an option for attaching the tightening device to a standing, in particular conventional, orthosis, in particular a knitted orthosis, and for removing the same therefrom, is no longer required; the tightening device according to the invention is rather an integral part of a corresponding novel orthosis according to the invention that is described herein.

In a special embodiment, the loose end of a cable leads into a handle, in which the cable is secured. The user can use the handle to tighten the loose end of the cable of a tackle assembly. The handle can be releasably secured in the region of the lateral element connected to the tackle assembly, which is to say in the region of the respective ends of the tightening device, so as to maintain the tension. The handle piece can comprise a clamping device in order to preset the length of the cable end. The "working point" of every tackle assembly can thus be set segmentally so as to assure the individual adaptation of the orthosis. The temporary fixation of the handle on the tightening device takes place in the manner that is known per se by way of hook-and-loop fastening or an interlaced connection.

In a special variant, the respective loose ends of the cables of the tackle assemblies of adjoining tightening segments are guided into a common handle and secured therein mutually spaced from each other. In this embodiment of the invention, the tension that is applied to the one or the other cable can be individually defined by pivoting or inclining the handle. To this end, the common handle can preferably be secured on the tightening device in the pivoted or inclined state. This improves the adjustability and operability of the tightening device even further. As an alternative, a preferably latchable reeling mechanism for the respective cables can be provided instead of a handle in the region of the lateral elements, the securing location of which can be varied.

The lateral element and/or central element comprise connecting means so as to be connected to the orthosis, optionally in a releasable manner. The invention thus also allows the tightening device to be added to and removed from an existing orthosis. The existing orthosis is in particular a conventional knitted orthosis, notably a rod orthosis, which due to the inherent elasticity thereof is guided around the body part and closed in the manner known per se by way of tabs. In the case of a back orthosis, the tightening device according to the invention can be added to the orthosis in the region of the back and the hip.

The tightening device according to the invention allows the tightening force of an orthosis to be individually adapted in a wide range. Because the stabilizing or immobilizing effect of the orthosis is essentially performed completely by the tightening device itself, an elastic knitted orthosis, which is located underneath and designed in the manner known per se, no longer needs to exert a complete tightening or supporting action. Thus, a knitted fabric can be advantageously employed, which can be used over a wide circumferential range, in the case of a back orthosis, for example, both with a thin waist and with a large abdomen or chest circumference, without having to provide knitted orthoses that are each individually adapted to the body size. The adaptation to the body circumference can in each case be carried out preferably solely by adjusting the tackle assemblies, which is to say in particular by way of the segmental adjustment of the "working points" of the loose ends of the tackle assemblies.

Another object of the invention is a cable clamp for individually clamping two cables in a common handle, in particular for use in connection with the tightening device according to the invention in one embodiment, in which at least two cable ends of two adjoining tackle assemblies end in the common handle at a distance from each other. According to the invention, the cable clamp is provided on or in the handle and allows the effective length of the cable of the tightening segment associated therewith to be adjusted individually and independently of the length of the cable of the adjoining tightening segment, so as to enable targeted pre-tensioning or relaxation of a particular tightening segment as compared to the adjoining tightening segment. The tightening device can thus be used to further improve the support function of an orthosis.

The cable clamp according to the invention comprises at least two mutually spaced cable holders, each for receiving a cable end. According to the invention, the cable holders are each designed so that they allow releasable clamping of the cable in the handle piece.

In a preferred embodiment, the clamping device comprises two mutually spaced cable holders so as to clamp two mutually spaced cables, respectively. For this purpose, the cable clamp is preferably designed as two pieces and is composed of a base element, having a cable holder formed therefrom, and a cap, which can be placed over the base element. In the joined state, the cap and base element are engaged so that the cable is releasably secured in the cable holder of the base element by way of clamping. For this purpose, the base element has at least one clamping cone, along which the cable is guided. This is preferably achieved by providing the clamping cone with an aperture or a bore, through which the cable is passed, so that the same, upon exiting the aperture or bore, can be guided along the surface of the clamping cone. In the assembled functional state of the clamping device, the clamping cone of the base body comes in contact and in engagement with a bore, groove, or cut-out provided in the cap, so that the cable that is guided along the clamping cone is fixed by way of clamping on the preferably structured surface thereof. To this end, the cap preferably comprises a conical bore, the dimensions of which correspond to the outer dimensions of the clamping cone of the base element.

So as to releasably secure the cap on the base body, the base body comprises at least one detent element having at least one catch, or preferably more catches, which engage correspondingly designed abutments in the cap and retain the cap on the base element against mechanical resistance and the action of an external force. The cap is pulled off counter to the mechanical resistance of the catch in the cap in order to detach the cap from the base element so as to adjust the cable length.

In a special embodiment of the handle for holding, the required clamping device is mounted in a pocket made of woven fabric. The pocket is closed for use of the handle, and the clamping device remains hidden during the use of the handle. The handle is secured to the orthosis or the tightening device by way of the handle pocket.

The invention will be described in more detail by the following drawings and description of the figures, without considering these as being limiting.

DETAILED DESCRIPTION OF THE INVENTION

Figure 1:
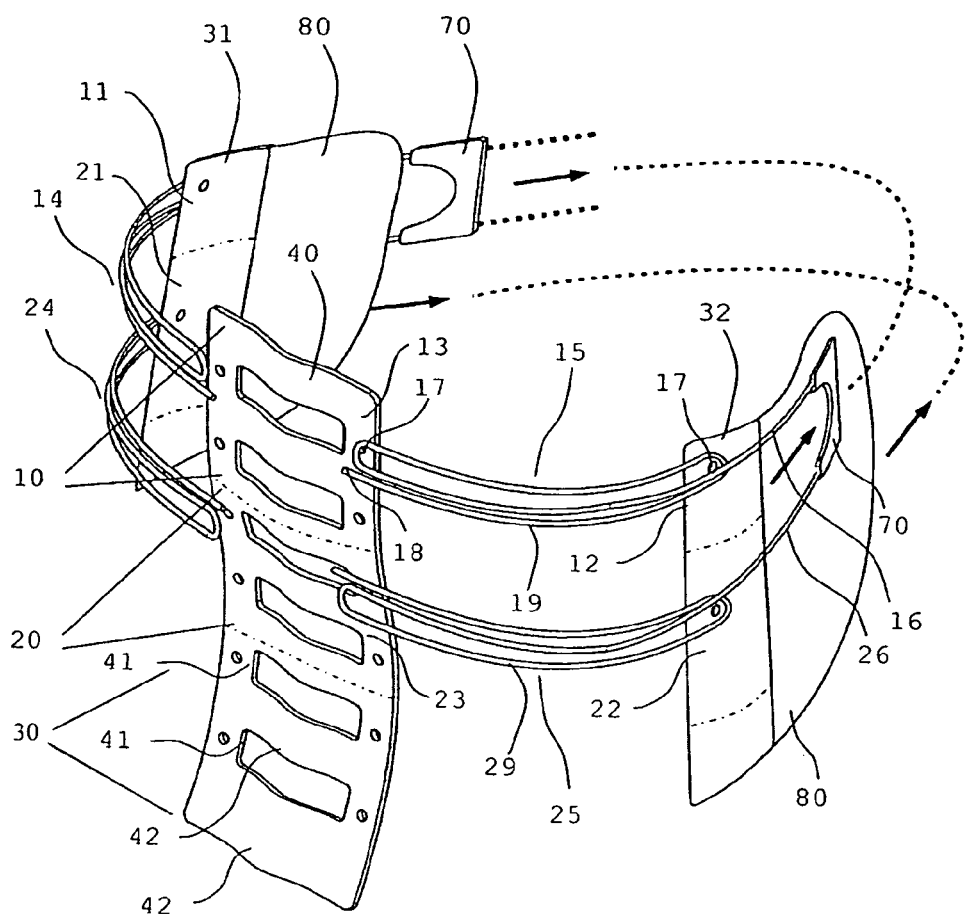
FIG. 1 is a perspective view of an embodiment of the tightening device according to the invention.

FIG. 1 shows an embodiment of the tightening device according to the invention, adapted for use on a back orthosis for stabilizing the spinal column. For clarity reasons, the view does not show all recurring structures in their entirety. Two cable drive mechanisms (14, 15) in the form of tackle assemblies are connected on each tightening segment (10) to the right and left of the central element (13), respectively, which are each mechanically connected to the lateral element (11), which in the figure is shown on the left and in the back, and the second lateral element (12), shown on the right and in the front. The tackle assembly (14, 15) comprises respective cable return points (17) and cable anchoring points (18), so as to form a multiple tackle assembly in each case. On each tightening segment, the tackle assembly (14, 15) is anchored on the central element (13) and lateral element (11, 12) in precisely one respective force application point (17, 18). In the figure, the lateral elements connected to form lateral bridges (31, 32) and the central elements connected to form a central bridge (40) are distinguished from each other by parting lines. The tackle assembly (14, 15) of the first tightening segment (10) each has loose cable ends (16), by way of which the tackle assembly can be tensioned, whereby the distance between the central element (13) and the respective lateral elements (11, 12) is shortened for tightening purposes.

The adjoining tightening segments (20) accordingly comprise a tackle assembly (24, 25) with cables (29) and loose ends (26). The tackle assembly (24, 25) in each case connects the first and second lateral elements (21, 22) to each other via the central element (23).

The separate tightening segments (10, 20), which are located below each other, are mechanically coupled to each other. To this end, in each case the first lateral element (11) of the first tightening segment (10) is coupled to the first lateral element (21) of the second tightening segment (20) to form a common integral lateral bridge (31). In a corresponding manner, the second lateral element 12 of the first tightening segment is coupled to the second lateral element (22) of the second tightening segment (20) to form an integral lateral bridge (32). Likewise, central element (13) of the first tightening segment (10) is coupled to the central element (23) of the second tightening segment (20) to form an integral central bridge (40). Despite mechanically coupling mechanical tightening segments (10, 20) to each other by way of the lateral bridges (31, 32) and the central bridge (40), a segmental individual adjustment of the tightening force is possible via the tackle assemblies that are separately guided in segments.

In the embodiment as back orthosis, the central bridge (40) forms a spinal column support that can be anatomically shaped and, when the orthosis is donned, is placed on or in the region of the spinal column. For this purpose, moreover, according to this embodiment, apertures (41) and, as an alternative or in addition, bulges (42) are provided in the central bridge (40) so as to distribute the pressure application of the spinal column to locations in regions to the left and right of the spinal column and prevent direct pressure application on the crests of the vertebrae.

The loose ends (16, 26) of the tackle assemblies of individual tightening segments (10, 20) on the right side and left side lead into a common handle (70) at a distance from each other. The handle (70) can be releasably secured in the region of the lateral elements/lateral bridges (11, 12, 31, 32). By pivoting the handle (70) during fixation, the tightening force can be individually distributed to the two tightening segments. In the embodiment shown, the formed lateral bridges (31, 32) each end in closing tabs (80), which are non-positively connected to each other when the orthosis is applied to the body in form of a belt or a bandage, whereby the segmental circular non-positive connection according to the invention is achieved.

Figure 2:
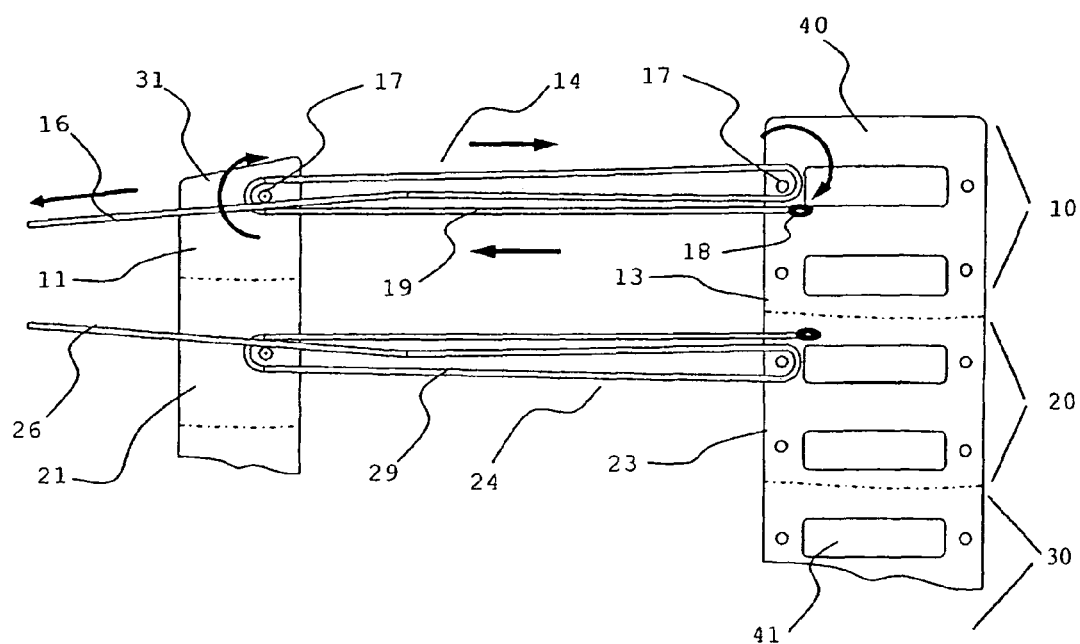
FIG. 2 is a schematic detailed illustration of a special embodiment of the tightening device of the invention.

FIG. 2 shows a schematic detailed illustration of a special embodiment of the tightening device according to the invention. Only one side (left side) of the tightening device is shown. The design of the tightening device to the right of the central element is mirror-symmetrical. The central elements (13, 23) of individual tightening segments (10, 20) are coupled to form an integral central bridge (40). The dotted parting lines show the coupling site tightening segments. In the illustration, the central bridge (40) is shown as one piece. The first lateral elements (11, 21) of the tightening segments (10, 20) are also coupled to form an integral lateral bridge (31). Exactly one tackle assembly (14) is formed between the central element (13) and the lateral element (11) on each tightening segment. A central element (13) and/or a lateral element (11) can provide alternative locations for the cable anchoring points (18) and cable return elements (17). In this way, individual adjustment of the pulling direction within each individual tightening segment is possible. The cables (19) of the tackle assembly (14) of the tightening segment (10) run in the immediate vicinity or on top of, but spatially separated and spaced from the cables (29) of the tackle assembly (24) of an adjoining tightening segment (20). For clarity reasons, the tackle assemblies of additional adjoining tightening segments are again not shown.

Figure 3:
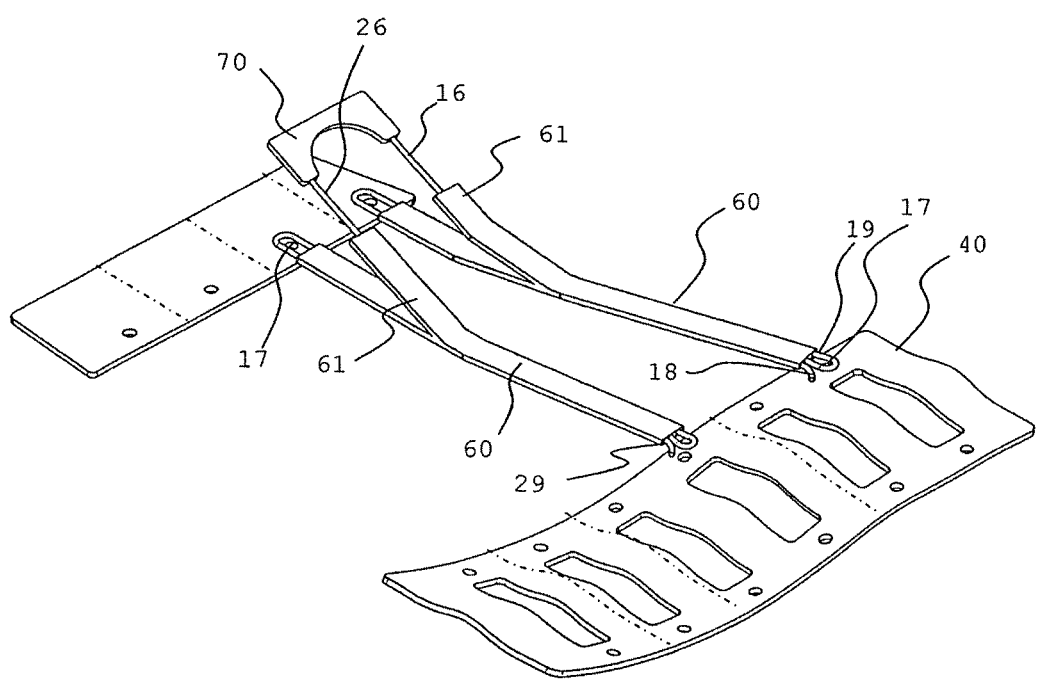
FIG. 3 is a perspective view of another embodiment of the tightening device of the invention.

According to FIG. 3, the cables (19, 29) are guided in respective cable tunnels (60). In the embodiment shown, the respective ends of the cables (19, 29) are guided out of the cable tunnels (60) so as to be guided over the cable returns (17) or anchored on the cable anchoring points (18). A respective tunnel branch (61) branches off each of the cable tunnels (60), with the respective cable ends (16, 26) being guided in the branch. In the form shown, these ends lead into a common handle (70) for tensioning the two cables.

Figure 4:
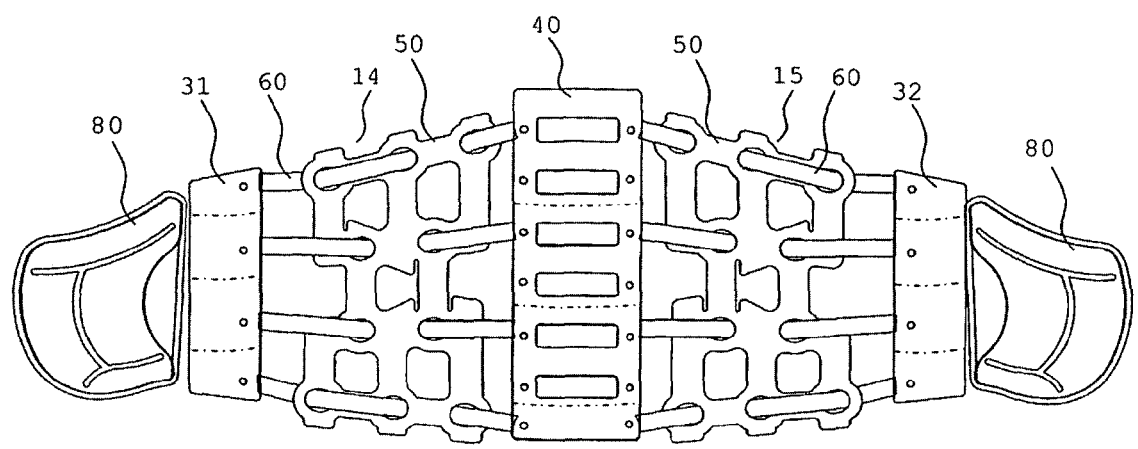
FIG. 4 is a schematic illustration of another special embodiment of the tightening device of the invention.

FIG. 4 is a schematic illustration of a special embodiment of the tightening device according to the invention, which can be added to a conventional knitted orthosis. The lateral elements, which are connected to form lateral bridges (31, 32), and the central elements, which are connected to form a central bridge (40), essentially form the mechanically rigid elements that preserve the overall structure of the tightening device. The central bridge (40) is also designed as a support element, which when the shown back orthosis is donned, is positioned on both sides of the vertebrae crests; this prevents direct pressure on the crests of the vertebrae. The cables of the tackle assembly (14, 15) extending from the central element to the lateral elements run in cable tunnels (60) made of elastic, flexible material. The cable tunnels are additionally guided through the lattice frames (50), which are arranged on both sides between the central elements and the lateral elements, and are held at a distance from each other. In the embodiment shown, the lattice frames (50) are made of rigid material and also serve as a pelvic support. The tightening device according to FIG. 4 ends in closing tabs (80) provided on both sides. These can be part of the tightening device itself or, alternatively, be a direct component of the conventional knitted orthosis to which the device can be added. In a special design of the embodiment according to FIG. 4, the tightening device, together with the closing tabs (80) connecting to the lateral bridges (31, 32) on both sides, can be used directly as an orthosis, without employing a conventional knitted orthosis located beneath. FIG. 4 thus shows an orthosis that can be used directly, which contains the tightening device according to the invention and essentially consists thereof.

Figure 5A:
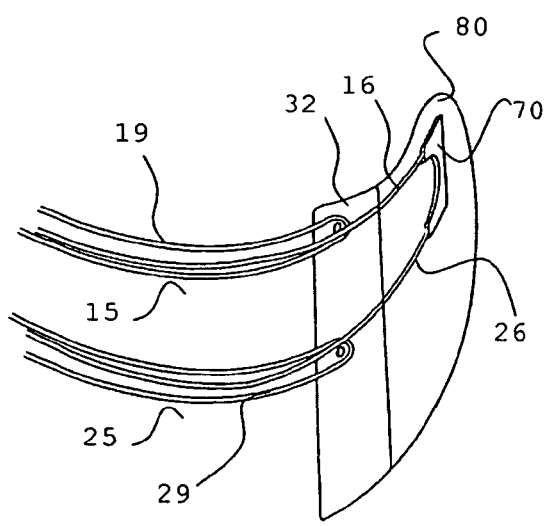
FIGS. 5A, 5B are detailed illustrations of the use of handles for simultaneously tightening the cables of the tackle assemblies of adjoining tightening segments.
Figure 5B:
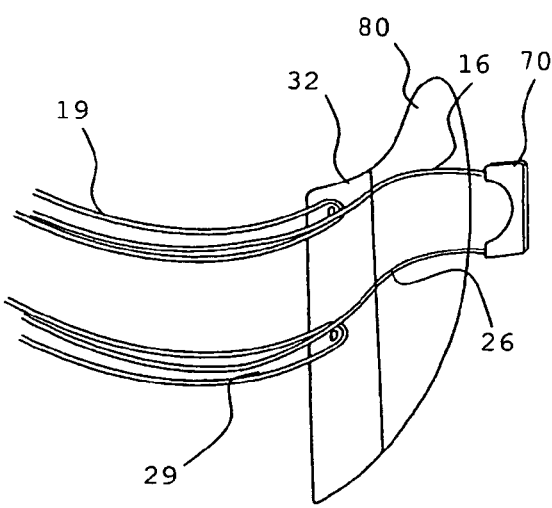

FIGS. 5A, 5B show detailed illustrations of the use of the handle (70) for simultaneously tightening the cables (19, 29) of the tackle assemblies (15, 25) of adjoining tightening segments by way of the loose ends (16, 26) thereof ending in a common handle piece (70). In the embodiment shown, in the tightened or released state, the handle (70) is releasably secured on the closing tab (80), which is associated with the lateral element (32) and mechanically connected thereto (FIG. 5A). The fixation is achieved, for example, via hooks that are present on the handle (70) on the side facing the closing tab (80) and engage the fabric surface of the closing tab (80). The handle (70) is lifted off the closing tab (80) for tightening or releasing the tension (FIG. 5B). If the tightening action of one of the two shown tightening sections is to be deliberately increased, the handle (70) is pivoted so that the pull at the respective loose end of the cable of the corresponding tightening segment is increased as compared to the pull on the loose end of the tackle assembly of the adjoining tightening segment, or the pull on the other loose end is decreased.

Figure 6:
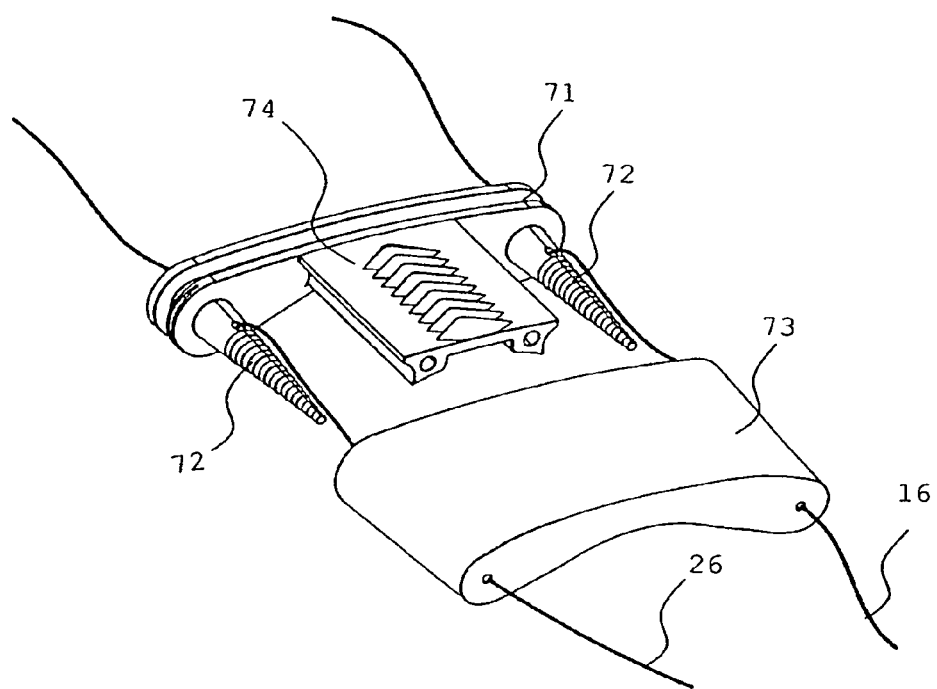
FIG. 6 is a detailed illustration of the handle as a clamping device for releasably securing the cable ends of two adjoining tackle assemblies.

FIG. 6 shows an embodiment of the handle (70) as a clamping device for releasably securing the cable ends (16, 26) of two adjoining tackle assemblies. The clamping device has a base element (71), on which two mutually spaced clamping cones (72) are formed. The clamping cones (72) comprise bores for receiving the cables. In addition, a cap (73) is provided, which is pushed over the base element (71), whereby the cables are clamped on the clamping cones (72). The cap (73) can be latched via a detent element (74) that is formed on the base body and abutments in the cap (73) which are designed in a corresponding manner (not shown).

The invention claimed is:

1. A tightening device for an orthosis, comprising
a plurality of separate tightening segments that can be independently tightened, each segment comprising
a first lateral element defining a first end of the tightening device,
a second lateral element defining an opposing second end of the tightening device,
a central element arranged between the first and second lateral elements, and
first and second tackle assemblies each comprising a respective cable,
wherein the first and second lateral elements of each of said tightening segments are connected to each other via the central element of that tightening segment by way of the first and second tackle assemblies, the first tackle assembly extending between the central element and the first lateral element, and the second tackle assembly extending between the central element and the second lateral element,
wherein the tackle assemblies are adapted to reduce distance of the lateral elements from each other thereby to effect said tightening, and
wherein the cable of each of the tackle assemblies has a loose end and pulling of the loose end effects said tightening.

2. The tightening device according to claim 1, wherein each of the tackle assemblies has at least one return for guiding the cable back in a direction from where the cable came and a cable anchoring point for anchoring an other end of the cable.

3. The tightening device according to claim 1, wherein each of the tightening segments comprises only one first tackle assembly and one second tackle assembly.

4. The tightening device according to claim 1, wherein the first lateral element of a first tightening segment is connected to the first lateral element of an adjoining second tightening segment to form a first integral lateral bridge, and the second lateral element of a first tightening segment is connected to the second lateral element of an adjoining second tightening segment to form a second integral lateral bridge.

5. The tightening device according to claim 1, wherein the central element of a first tightening segment is connected to the central element of an adjoining second tightening segment to form an integral central bridge.

6. The tightening device according to claim 1, wherein the cables of the first and second tackle assemblies of a first tightening segment are spaced from the respective cables of the first and second tackle assemblies of an adjoining second tightening segment.

7. The tightening device according to claim 6, wherein the respective cables of the first and second tackle assemblies run in respective lattice frames arranged between the central element and the respective first and second lateral elements.

8. The tightening device according to claim 1, wherein the respective cables of the respective first and second tackle assemblies run in respective first and second cable tunnels that extend between the respective first and second lateral elements and the central element and are made of plastic flexible material.

9. The tightening device according to claim 8, wherein the cable tunnel has a tunnel branch, in which the loose end of the cable is guided.

10. The tightening device according to claim 1, wherein the loose end of the cable leads into a handle for tightening the cable and is secured therein, wherein the handle is releasably secured on or adjacent the tightening device.

11. The tightening device according to claim 10, wherein the handle has a clamping device that is adapted to pre-set length of the cable.

12. The tightening device according to claim 1, wherein the respective loose ends of the cables of the tackle assemblies of adjoining first and second tightening segments lead into a common handle and are secured therein at a distance from each other, so as to allow the pull on the tackle assembly associated with the first tightening segment and the tackle assembly associated with the second tightening segment to be individually distributed by pivoting or inclining the common handle.

13. The tightening device according to claim 1, further comprising a releasable mechanical coupling in a region of the lateral elements and/or of the central element for securing the tightening device to a knitted orthosis.

14. An orthosis, comprising the tightening device according to claim 1.

15. A method of selectively and independently tightening segments of an orthosis, comprising using the tightening device according to claim 1.

16. A tightening device for an orthosis, comprising
a plurality of separate tightening segments that can be independently tightened, each segment comprising:
a first lateral element defining a first end of the tightening device;
a second lateral element defining an opposing second end of the tightening device;
a central element arranged between the first and second lateral elements; and
first and second tackle assemblies each comprising a respective cable; and
wherein the first and second lateral elements of each of said tightening segments are connected to each other via the central element of that tightening segment by way of the first and second tackle assemblies, the first tackle assembly extending between the central element and the first lateral element, and the second tackle assembly extending between the central element and the second lateral element; and
wherein the first lateral element of a first tightening segment is connected to the first lateral element of an adjoining second tightening segment to form a first integral lateral bridge, and the second lateral element of a first tightening segment is connected to the second lateral element of an adjoining second tightening segment to form a second integral lateral bridge.

17. A tightening device for an orthosis, comprising
a plurality of separate tightening segments that can be independently tightened, each segment comprising:
a first lateral element defining a first end of the tightening device;
a second lateral element defining an opposing second end of the tightening device;
a central element arranged between the first and second lateral elements;
first and second tackle assemblies each comprising a respective cable; and
a releasable mechanical coupling in a region of the first and second lateral elements and/or of the central element for securing the tightening device to a knitted orthosis; and
wherein the first and second lateral elements of each of said tightening segments are connected to each other via the central element of that tightening segment by way of the first and second tackle assemblies, the first tackle assembly extending between the central element and the first lateral element, and the second tackle assembly extending between the central element and the second lateral element.

* * * * *